(12) United States Patent
Dale et al.

(10) Patent No.: US 9,791,401 B2
(45) Date of Patent: Oct. 17, 2017

(54) DEVICE INCLUDING BIOSENSOR AND HOLDER

(71) Applicant: SARISSA BIOMEDICAL LIMITED, Coventry (GB)

(72) Inventors: Nicholas Dale, Coventry (GB); Faming Tian, Coventry (GB)

(73) Assignee: SARISSA BIOMEDICAL LIMITED, Coventry (GB)

(*) Notice: Subject to any disclaimer, the term of this patent is extended or adjusted under 35 U.S.C. 154(b) by 156 days.

(21) Appl. No.: 14/649,993

(22) PCT Filed: Nov. 28, 2013

(86) PCT No.: PCT/GB2013/053150
§ 371 (c)(1),
(2) Date: Jun. 5, 2015

(87) PCT Pub. No.: WO2014/087137
PCT Pub. Date: Jun. 12, 2014

(65) Prior Publication Data
US 2015/0316500 A1   Nov. 5, 2015

(30) Foreign Application Priority Data

Dec. 7, 2012 (GB) .................. 1222074.5

(51) Int. Cl.
*G01N 27/327* (2006.01)
*A61B 10/00* (2006.01)
(Continued)

(52) U.S. Cl.
CPC ....... *G01N 27/327* (2013.01); *A61B 10/0096* (2013.01); *C12Q 1/003* (2013.01);
(Continued)

(58) Field of Classification Search
CPC ............ G01N 27/327; G01N 27/3271; G01N 27/3272; G01N 35/025; G01N 35/026; G01N 35/028; G01N 2223/307
See application file for complete search history.

(56) References Cited

U.S. PATENT DOCUMENTS 3,429,785 A * 2/1969 Ross .................. G01N 27/3335
204/295
3,979,274 A * 9/1976 Newman ................. C12Q 1/002
156/230
(Continued)

FOREIGN PATENT DOCUMENTS

FR          2777996       10/1999
WO       2008/081193      7/2008

OTHER PUBLICATIONS

International Search Report prepared for PCT/GB2013/053150, dated Mar. 25, 2014.
(Continued)

*Primary Examiner* — Alexander Noguerola
(74) *Attorney, Agent, or Firm* — Brannon Sowers & Cracraft PC

(57) ABSTRACT

A device utilizing biosensors to enable rapid electrochemical sensing of one or more analytes in a container. The device comprises a holder which incorporates at least one reference electrode and at least one sensing electrode. The sensing electrode comprising an electrically conductive substrate which is coated in a first layer of a suitable electron acceptor and subsequently with a second layer incorporating a biorecognition molecule adsorbed or within a suitable electropolymer matrix or carrier.

20 Claims, 2 Drawing Sheets

(51) Int. Cl.
  *G01N 33/543* (2006.01)
  *C12Q 1/00* (2006.01)
  *B01L 3/00* (2006.01)

(52) U.S. Cl.
  CPC ..... *G01N 27/3271* (2013.01); *G01N 33/5438* (2013.01); *B01L 3/5021* (2013.01); *B01L 3/50825* (2013.01); *B01L 2300/046* (2013.01); *B01L 2300/0636* (2013.01); *B01L 2300/0645* (2013.01); *G01N 2223/307* (2013.01); *G01N 2800/2871* (2013.01); *G01N 2800/302* (2013.01)

(56) References Cited

U.S. PATENT DOCUMENTS

| | | | | |
|---|---|---|---|---|
| 4,048,040 A | * | 9/1977 | Schwartz | G01N 33/49 204/400 |
| 4,322,279 A | * | 3/1982 | Piper | G01N 27/30 204/403.01 |
| 4,869,133 A | * | 9/1989 | Irazoqui | B67B 7/02 81/3.08 |
| 5,582,696 A | * | 12/1996 | Sheehan | C12Q 1/006 204/403.06 |
| 5,951,524 A | * | 9/1999 | Enriquez | B01L 9/06 604/192 |
| 2005/0023672 A1 | | 2/2005 | Oostman | |

OTHER PUBLICATIONS

Tian, Fanning, Enrique Llaudet, and Nicholas Dale. "Ruthenium purple-mediated microelectrode biosensors based on sol-gel film." Analytical chemistry 79.17 (2007): 6760-6766.

Dill, Kilian, and Andrey Ghindilis. "Electrochemical detection on nnicroarrays." Microarrays. Springer New York, 2009. 25-34.

* cited by examiner

DEVICE INCLUDING BIOSENSOR AND HOLDER

CROSS-REFERENCE TO RELATED APPLICATIONS

This application is a U.S. national application under 37 C.F.R. §371(b) of International Application Serial No. PCT/GB2013/053150 filed Nov. 28, 2013, which claims priority under 35 U.S.C. §119(e) to GB Patent Application No. 1222074.5 filed on Dec. 7, 2012, the entire disclosures of which are incorporated herein by reference.

The present invention relates to a biosensor device for containers or supports for biological samples, for example vacutubes, for use in rapid electrochemical sensing of one or more analytes. Also provided are kits containing said devices, and their uses in rapid electrochemical sensing of analytes in biological samples.

BACKGROUND OF THE INVENTION

There is a need for more rapid ways of measuring and monitoring the presence and concentration of analytes in biological samples for example in the diagnosis or monitoring of medical conditions or physiological states in biological systems.

In the field of medicine, the point of sampling from a human or animal subject is often also a point of care, for example the subject is in the presence of a health professional ready to take steps depending on the result of the analytical outcome. The time taken for a biological sample to be transported from its collection point, say a point of care (e.g. doctor surgery or clinic, hospital bedside, operating theatre), to a suitable laboratory or dedicated laboratory area can amount to significant delay. With each additional handling and transport step taking several minutes or longer, it can be a matter of hours or more before a relevant result or reading is available from any given sample, especially where analytical techniques requiring further sample preparation e.g. HPLC are involved.

Biosensors are valuable tools in the measurement of a wide range of analytes in biological samples. A typical biosensor comprises a sensing electrode having a biorecognition molecule, such as an antibody or enzyme, attached to a transducer so as to enable detection of the binding of an analyte to the biorecognition molecule. Examples of transducers for biosensors include electrochemical, piezoelectric, optoelectronic, fibre optic, thermistor, diode or acoustic devices. A wide range of compounds and polymers can be used to enable the transfer of electrons between a suitable biorecognition molecule and an electrically conductive substrate.

Entrapment of biorecognition molecules in electropolymer matrices has enabled the construction of biosensors with very small and custom shaped sensing elements. For example WO 2003/087801, describes biosensors and methods for producing biosensors for use in detecting and monitoring purines such as adenosine. These comprise a substrate comprising platinum or a platinum alloy; a first layer formed on the substrate comprising a sugar-derivative of a pyrrole and a second layer formed on the first layer comprising an amphiphilic pyrrole and one or more enzymes within the second layer. WO 2004/048603, describes methods of producing sol-gels on electrically conductive substrate to allow the entrapment of, for example, enzymes into a sol-gel matrix for the production of biosensors. Such micro-sensors are minimally invasive and have been used for detecting neurotransmitter release in the central nervous system. The microelectrodes are made from platinum or platinum alloy wire with all but about the final 2 mm of the Pt wire protected by a pulled glass capillary that is fused to the wire using heat. The exposed sensing tip suitably has a diameter from 25 to 100 um. These micro-sensors are fragile and the tips in particular require careful handling so as not to damage the sensing tip.

WO 2008/081193, incorporated herein, describes a biosensor comprising an electrically conductive substrate, with a first layer comprising Ruthenium Purple formed on the substrate, a second layer comprising polyaniline or a derivative thereof comprising one or more non-polar substituents formed on the first layer, and a third layer comprising one or more enzymes trapped within a matrix formed on the second layer. An advantage of using Ruthenium Purple, $KFeRu(CN)_6$ or $Fe_4[Ru(CN)_6]_3$, is that it allows small/micro biosensors to be formed, for example biosensors which are about 50 µm diameter and 0.1 to 2 mm in length. Preferred miniature biosensors are, for example less than 25 µm diameter and about 300 µm to about 2 mm long. Such biosensors are of particular use in the detection of analytes such as purines and derivatives thereof, particularly hypoxanthine. In operation, such biosensors are stable for several hours.

SUMMARY OF THE INVENTION

The present invention now provides biosensor devices for containers or supports for biological samples so that rapid or 'point of care' measurements of sample analytes can be made using electrochemical biosensor probes.

Accordingly, in a first aspect the present invention provides a device for a container or support for receiving a biological sample for use in rapid electrochemical sensing of one or more analytes using biosensors, wherein the device comprises a holder for holding at least one sensing electrode and at least one reference electrode, the or each sensing electrode and the or each reference electrode being held and protruding from a sample receiving surface of the holder, the or each sensing electrode comprises an electrically conductive substrate comprising platinum, platinum alloy, gold, gold alloy or carbon, with a first layer on the substrate comprising a suitable electron acceptor, and a second layer comprising a biorecognition molecule adsorbed or within a suitable electropolymer matrix or carrier.

In one embodiment of the invention, the device forms part of a closure for the container or support. In another embodiment, the device forms part of a cap for a vacutube or vacutainer.

In a further embodiment the holder may comprise 2, 3, 4, 5, or 6 sensing electrodes. In another embodiment the electron acceptor is Ruthenium Purple (RP)

In one embodiment the electrically conductive substrate surface comprises gold of at least 18 carat purity. In a further embodiment, the electrically conductive substrate surface comprises a platinum alloy with a 90:10 ratio of platinum:iridium (weight:weight).

In another embodiment, the electropolymer matrix material comprises a sol-gel, such as a sol-gel comprising a mercaptan containing silane and/or a bifunctional silane. In a further embodiment, the or each sensing electrode incorporates an intermediate layer between the electron acceptor and the electropolymer matrix or carrier, whereby the intermediate layer comprises a polyaniline or a derivative thereof comprising one or more non-polar substituents In one embodiment of the invention the analytes are biomarkers selected from one or more of hypoxanthine, adenosine, ATP, inosine, acetylcholine, choline, glucose, glutamate, lactate and D-serine. In a further embodiment, the biorecognition molecule is an antibody or enzyme. In another embodiment, the analytes provide indicators of biochemical abnormalities for use in diagnostic or monitoring purposes or indicators of physiological condition in healthy organisms.

In yet another embodiment, the holder comprises more than one type of sensing electrode for the analysis of more than one analyte.

In another aspect of the invention the device forms part of a cap for a vacutube or vacutainer. In a further aspect of the present invention, a kit is provided for the detection of one or more analytes. In one embodiment the kit is for use in foetal monitoring, stroke monitoring, or schizophrenia diagnosis. In a further embodiment, the kit is for home or mobile applications.

In a further embodiment, the device, cap or kit may be for single or disposable use.

Another aspect of the invention provides the use of the device, cap or kit in the detection of one or more analytes. In another embodiment, the device, cap or kit may be used whereby at least one analyte has a half-life in the biological sample of less than 10 mins.

A further aspect of the invention provides a method of preparing a device according to any preceding claim comprising the steps of:
i) providing a substrate comprising an electrically conductive substrate surface within a holder;
ii) depositing a first layer comprising a suitable electron acceptor;
iii) depositing a second layer, the second layer comprising an electropolymer matrix with one or more biorecognition molecules absorbed on or included within said second layer.

In one embodiment, a method is provided whereby the first layer comprising a suitable electron acceptor is protected by deposition of a polyaniline layer, or a layer comprising a polyaniline derivative comprising one or more non-polar substituents, before the deposition of the second layer comprising an electropolymer matrix.

The arrangement of the sensing and reference electrodes in the device is such that once the support or container and device are assembled and positioned as necessary, contact is made with the sample so that rapid readings can be taken.

A major advantage of devices according to the present invention is in enabling measurements of multiple analytes in a single sample. Particularly useful are devices according to the present invention using miniaturised biosensors which can be used with very small samples, or volumes as small as a drop or a few ul.

For example, when used to monitor hypoxanthine as an indicator of a baby's level of oxygen during birth, drops of blood can be taken from the baby's scalp while still in the womb and placed on the device for measurement.

Biological materials that can be analysed according to the invention include fluids and mixtures of fluids, cells or particulate matter. Examples include blood, serum, urine, cerebrospinal fluid, plasma, tears, sweat and other secretions, suitable digestive contents and the like.

The type of support or container for the collection of samples will depend on the type of analysis and the type of any additive, if used. Known in the art are containers, typically tubes, which contain a vacuum or partial vacuum so that when the sample source is connected to the container, say via a needle or siphon, the pressure difference between the container and the biological fluid causes the fluid to flow into the container.

Where small samples or volumes of samples are involved it may be necessary or advantageous to tilt or invert the assembly to facilitate contact of the electrodes with the sample. For example, where the device of the invention is incorporated or fits within a cap for a tube or container, the cap provides a seal which allows the tube to be tilted or mixed (if necessary) and inverted. In one embodiment the device further comprises a spacer of suitable or inert material providing a seal or closure and allowing the tube or container to be tilted or inverted so as to retain the sample.

For blood or other fluid containing cells or particles, the collection container may include a gel to separate the various fractions. After settling or centrifugation the cells or particles go to the bottom of the container and the fluid or serum to the top. For example where the fluid is blood, a gel can be used which has a density intermediate between blood cells and serum and so can be used to separate these.

A further aspect of the present invention provides a cap including a device according to the present invention which can be used or adapted for use with conventional blood sampling tubes as used by healthcare professionals and practitioners worldwide.

Containers specifically designed for capillary or venous blood collection include 'Vacutubes' [Trade mark of Becton Dickinson & Co.] or 'Vacutainers [Trade Mark]' as available from Becton Dickinson, www.bd.com. Other suppliers include International Scientific Supplies Ltd, www.intscientific.com. The caps of blood vacutubes are colour coded according to a standard adopted by manufacturers. For example tubes with a normal vacuum have opaque caps, tubes for small or delicate veins are translucent. The tubes may contain anticoagulants such as heparin (green caps), EDTA (purple or lavender caps) or sodium citrate (light blue caps). Others contain preservatives. Where more than one tube is to be filled at a time, a specific order of tubes needs to be followed as the needles can carry additives from one tube to the next and might otherwise interfere with some analyses. A typical sample size collected would be in the order of 5 ml. Custom tubes for collecting smaller samples of say 0.5 ml can also be used and smaller caps containing devices according to the invention provided accordingly.

A preferred embodiment of the present invention is a cap for a vacutube. For example, once the sample has been taken, the existing vacutube cap can be removed and replaced by a cap according to the present invention so as to allow a rapid biosensor analysis to take place.

The particular benefit of having rapid or 'point of care' results is clear where the timing of a decision or diagnosis is critical and needs to be determined in a few minutes rather than hours or longer. Even if timing not critical, the availability of early results allows more efficient use of healthcare professional time as relevant advice can be given straightaway, so avoiding a subsequent appointments or visit for reviewing results.

Rapid analyses made possible according to the invention will be of particular benefit in the detection, diagnosis and treatment of a number of medical conditions. For example in stroke and the detection of foetal hypoxia in childbirth. In addition, rapid analyses are advantageous in situations where the analyte rapidly degrades in the isolated biological sample, for example ATP, adenosine, inosine or hypoxanthine.

Apart from applications in medicine and healthcare, it is also useful to be able to make rapid measurement of metabolites in healthy subjects, e.g. lactate or glucose levels during performance in animals, including humans.

The measurement of multiple analytes (such as the purines adenosine, inosine, hypoxanthine) is particularly useful in the detection and monitoring of stroke (brain hypoxia and ischaemia), mini-strokes (transient ischaemic attack or TIA). The measurements of such analytes may also be useful for brain hypoxia/ischaemia arising from conditions other than stroke e.g. during clinical procedures, following traumatic brain injury The ability to measure D-serine is particularly useful in the diagnosis of schizophrenia.

The ability to measure and monitor the levels of purines such as hypoxanthine can be particularly valuable. Hypoxanthine can provide an indicator of a baby's oxygen levels during birth and as such acts as an early warning system for distress. Foetal hypoxia, or oxygen starvation, can result in cerebral palsy or other biological defects for a child. If a baby's brain is being starved of oxygen, midwives and doctors can make a more informed decision on the necessity of a caesarean operation or section. A baby with more than 5 uM of hypoxanthine per liter of blood is at severe risk of foetal hypoxia. A level of 15 uM or more could indicate major hypoxia and a heightened risk of brain damage. Monitoring hypoxanthine levels can therefore help to prevent unnecessary or precautionary emergency caesarean sections.

At present, blood samples are routinely taken from the delivery or operating room to a laboratory or separate laboratory area for analysis, which causes an inherent delay in obtaining the results. Therefore, a particular advantage of the present invention is in enabling a biosensor system able to give doctors in the delivery or operating room almost instant data on whether an unborn child faced the risk of hypoxia.

Examples of analytes and enzymes used for their detection for use in the present invention include: hypoxanthine (xanthine oxidase), lactate (lactate oxidase or L-lactate dehydrogenase and glutamic pyruvic transaminase), creatine (creatininase and creatinase and sarcosine oxidase), glucose (glucose oxidase), cholesterol (cholesterol oxidase), galactose (galactose oxidase), glutamate (glutamate oxidase or L-glutamate dehydrogenase), glutamine and glutamate (glutaminase or glutamate oxidase), hydrogen peroxide (horse radish peroxidise), fructose (D-fructose dehydrogenase), ethanol (alcohol dehydrogenase), methanol (methanol dehydrogenase), urea (urease), and uric acid (uricase and horse radish peroxidase) D-amino acid oxidase, glycerol-3-phosphate oxidase, glycerol kinase, adenosine deaminase, purine nucleoside phosphorylase, acetylcholinesterase, and choline oxidase.

Suitably the analytes are biomarkers. Biomarkers provide indicators of biochemical abnormalities for use in diagnostic or monitoring purposes, and include for example the analytes purines and derivatives thereof, for example hypoxanthine, adenosine, ATP, inosine, acetylcholine, glucose, glutamate, hypoxanthine, lactate and D-serine.

The invention will now be described by way of example only, with reference to the following Figures and Examples, which are intended to be illustrative only, and in no way limiting on the scope of invention.

DETAILED DESCRIPTION OF THE INVENTION

Figure 1:
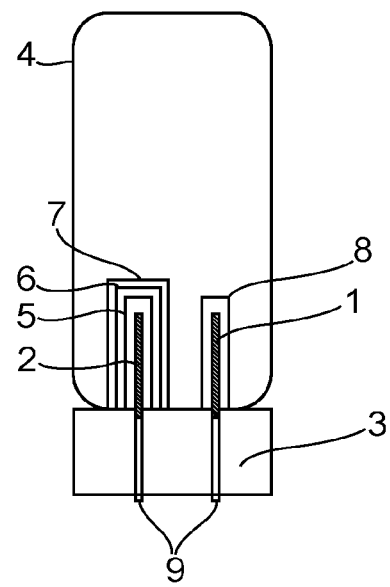
FIG. 1: Shows a schematic cross-sectional representation of a device for a container.

Referring to FIG. 1, the device encompasses at least one reference electrode (1) and at least one sensing electrode (2). The device may comprise 2, 3, 4, 5 or 6 sensing electrodes. In one embodiment of the invention the device comprises four sensing electrodes. In a further embodiment the device comprises four sensing electrodes and two reference electrodes.

The electrodes are incorporated into the holder (3) and protrude into the interior of the container (4). It will be appreciated by the skilled reader that the protrusion of the electrodes into the container is sufficient so that they are in contact with any biological sample within the container. In one embodiment the protrusion of the electrodes is in the range 10 to 150 µm. In a further embodiment the protrusion is around 100 µm. It will also be appreciated that the container could be inverted or tilted to enable this contact to be made, and therefore that the device may seal the container to enable inversion with retention of the contents. In one embodiment of the invention the device forms part of a cap for a container. In a further embodiment, the device forms part of a cap for a vacutube or vacutainer. In another embodiment, the device is a cap for a vacutube.

Each sensing electrode (2) comprises an electrically conductive substrate, which may be made from platinum, platinum alloy, gold, gold alloy or carbon. In one embodiment the substrate comprises gold wire. In another embodiment of the invention this substrate comprises gold of at least 18 carat purity. In a further embodiment the substrate comprises a platinum alloy with a 90:10 ratio of platinum:iridium (weight:weight).

This substrate is coated in a first layer (5) which comprises an electron acceptor and a second layer (7) which comprises a biorecognition molecule adsorbed or within a suitable electropolymer matrix or carrier. In one embodiment of the invention the electron acceptor for the first layer is ruthenium purple, $KFeRu(CN)_6$ or $Fe_4[Ru(CN)_6]_3$. In a further embodiment, the electron acceptor is ruthenium purple and the electropolymer matrix or carrier comprises a sol-gel. In a further embodiment the sol-gel comprises one or more silicon based compounds. In another embodiment the sol-gel comprises a mercaptan containing silane and/or a bi-functional silane.

The biorecognition molecule may be, for example, an antibody or an enzyme. Suitable antibodies or enzymes include those which recognise biomarkers, for example hypoxanthine, adenosine, ATP, inosine, acetylcholine, choline, glucose, glutamate, lactate and D-serine. Purines such as adenosine, inosine and hypoxanthine are suitable biomarkers for the indication of a stroke or Ischaemia. Different purines plus glutamate and/or D-serine are combinations that may be used to try to discriminate different sources of ischaemia.

It will be appreciated by the skilled person that the device is suitable for the electrochemical sensing of analytes with a range of half-life values, including those with a short half-life in the biological sample, for example ATP, adenosine, inosine or hypoxanthine. Analytes with a short half-life in the biological sample include those with a half-life of less than 5 minutes, for example less than 2 minutes, less than 1 minute, less than 30 seconds and less than 15 seconds.

An additional layer (6) may be used between the first layer comprising an electron acceptor (5) and the second layer comprising a biorecognition molecule adsorbed or within a suitable electropolymer matrix or carrier (7). The additional layer (6) may function to protect and preserve the electron acceptor. In one embodiment the additional layer comprises a polyaniline. In a further embodiment the additional layer is a derivative of a polyaniline comprising one or more non-polar substituents.

Figure 2:
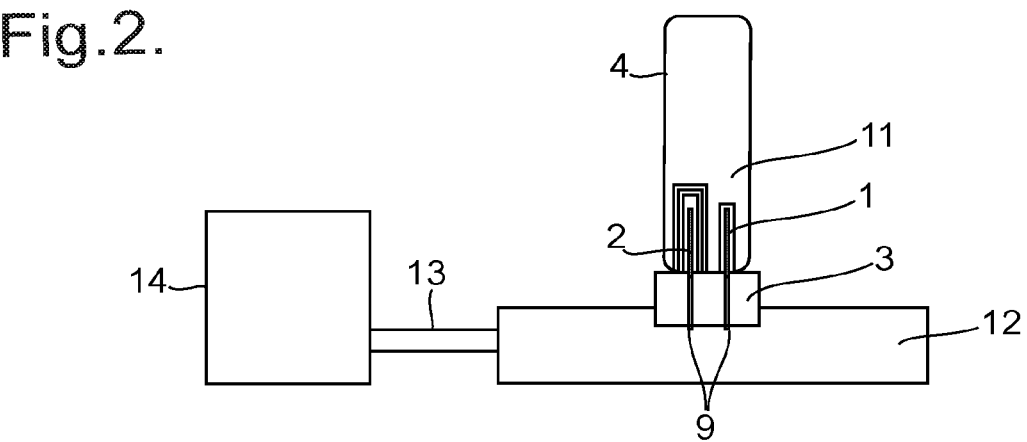
FIG. 2: Shows a schematic cross-sectional representation of a device connected to a measurement apparatus for the detection of an analyte.

It should be noted that the relative dimensions of the electrodes and the layers coating the electrodes are as shown in FIGS. 1 and 2 for ease of illustration only.

More than one sensing electrode may be used to allow measurement of more than one analyte simultaneously, and to incorporate control sensors that lack the enzymes to detect specific analytes thus increasing the quality of the data. It will be appreciated that, in order to enable the simultaneous detection of more than one analyte, the sensing electrodes may comprise different bio-recognition molecules.

The at least one reference electrode (1) is made from an electrically conductive substrate. The electrically conductive substrate may be coated to form a layer (8). In one embodiment the reference electrode comprises a silver wire. In a further embodiment the reference electrode is silver wire coated with AgCl. The at least one reference electrode (1) and at least one sensing electrode (2) may comprise different electrically conductive substrates. In one embodiment of the invention the at least one reference electrode comprises silver wire and the at least one sensing electrode comprises gold wire. In one embodiment of the invention the diameter of the wire is in the range 150-250 µm. In a further embodiment the diameter of the wire is around 200 µm. The electrodes are attached to supporting legs (9) which are embedded within the holder (3). It will be understood by the skilled person that the supporting legs are made from an electrically conductive substrate. In one embodiment of the invention the supporting legs are made from a nickel alloy.

The holder (3) comprises an inert and insulating material. In one embodiment of the invention the cap comprises a polyurethane resin.

Referring to FIG. 2, the at least one reference electrode (1) and the at least one sensing electrode (2) are positioned by the holder (3) to protrude into the interior of the container (4) and to make contact with a biological sample (11). The holder additionally enables electrical connection of the electrodes (1, 2), via the supporting legs (9) to a docking station (12) which in turn connects the electrodes via wires (13) to a measuring device (14).

Each sensing electrode is connected to one channel on the docking station. A further channel is required for the reference electrodes. Each channel is connected to a measuring device (14). In one embodiment of the invention the measuring device is a potentiostat able to measure currents in the pA to nA range. One skilled in the art would understand that said potentiostat should be capable of at least two-electrode operation.

EXAMPLES

Figure 3:
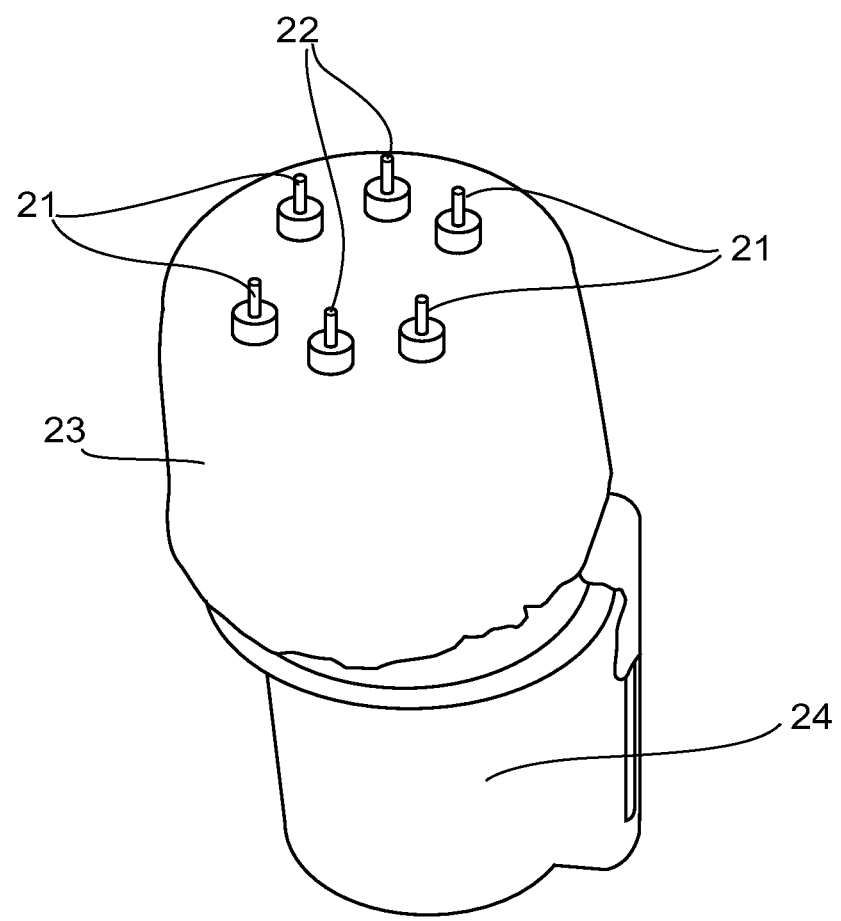
FIG. 3: Shows a picture of a polyurethane moulded cap.

Formation of a Cap with Integrated Sensing and Reference Electrodes
(A) Moulding of a Polyurethane Cap An example of a polyurethane cap is shown in FIG. 3. This picture shows gold wire tipped legs (21), silver wire tipped legs (22), a polyurethane cap (23) and a supporting collar (24).

Gold wire is attached to four nickel alloy legs (length 2.5 cm) and silver wire is attached to two nickel alloy legs (length 2.5 cm). The six legs are placed in a supporting collar (24) which aligns the legs with holes in the bottom of a mould. The mould defines the shape of the cap and has three holes on each side to correspond to the desired position of the electrodes. The legs are positioned so that there is one silver wire tipped leg (22) and two gold wire tipped legs on each side (21), with the silver wire tipped electrodes in the central position.

Fast casting polyurethane resin (approximately 1.5 mL) is injected into the mould using a syringe. The cap (23) is then removed from the mould after a period of 15 minutes at room temperature and then cured for a period of one day.
(B) Electrodeposition of Silver Chloride onto the Surface of the Silver Wire Electrodes.

The cap is connected to a multi-socket board and then dipped into an electrochemical bath containing AgCl in HCl (1 M). The electrochemical bath is equipped with a Pt foil counter electrode and a Ag/AgCl reference electrode. A constant galvanostatic current of 10 mAcm$^{-2}$ is applied to anodically plate the silver wire with AgCl.
(C) Electrodeposition of Ruthenium Purple (RP) on the Surface of the Gold Wire Electrodes.

The cap connected to a multi-socket board is dipped into an electrochemical bath, equipped with a Pt foil counter electrode and a Ag/AgCl reference electrode, and filled with a mixture of $FeCl_3$ (1 mM) KCl (40 mM, pH 2), $K_4Ru(CN)_6$ (1 mM) and KCl (40 mM, pH 2). The channels connected to the gold wires are subjected to scanning cyclic voltammetry from −0.2 to +0.7 V for forty cycles at 50 mV/s. The resulting ruthenium purple modified cap is heated at 80 degrees for 12 hours. The cap is further subjected to scanning cyclic voltammetry (2-4 cycles, −0.2 to +0.7 V at 50 mV/s) in a solution of $RuCl_3$ (1 mM containing 1 mM KCl, pH2) to further stabilize the ruthenium purple film on the gold wires.
(D) Formation of a Polyaniline Layer.

In examples where a polyaniline layer is used, the ruthenium purple modified gold wires are dipped into an electrochemical bath containing 10 mM aniline plus 0.5 M $H_2SO_4$ and 0.5 M KCl, followed by electrochemical cycling between −0.2 and +1.3V for 7 cycles at 100 mV/s.
(E) Electrodeposition of a Sol Gel Layer.

The multi-socket board is transferred onto a multiwall plate, which is filled with pre-hydrolysed silane mixture either with or without desired enzymes. The central AgCl coated silver wire on each side of cap is employed as reference and counter electrode for gel formation on ruthenium purple modified gold wires. The sol gel layers are preferably entrapped by electro-deposition at −0.9 to +1.3 V or 6 µA for 10 to 30 seconds.

Formation of a Cap with Different Sensing Electrodes

Formation of a cap with more than one type of biosensor may be carried out by the control of the circuit to each sensing electrode during the electrodeposition of the sol gel layer. The gold wires are connected and controlled with different channels of a multi-socket board. Each channel may be switched on forming a biosensor on the surface of a specific gold wire. Different types of biosensor can therefore be prepared using a series of pre-hydrolysed silane mixtures with different enzymes and applying appropriate potential or current through each circuit in turn.

The invention claimed is:

1. A device for a container or support, where the container or support is capable of or adapted for receiving a biological sample for use in rapid electrochemical sensing of one or more analytes using biosensors,
   wherein the device forms at least part of a closure for the container or support and the device comprises a holder for holding at least one sensing electrode and at least one reference electrode, the or each sensing electrode and the or each reference electrode being held and protruding from a sample receiving surface of the holder, and
   where the or each sensing electrode comprises an electrically conductive substrate comprising platinum, platinum alloy, gold, gold alloy, or carbon, with a first layer on the substrate comprising an electron acceptor, and a second layer comprising a biorecognition molecule adsorbed or within an electropolymer matrix or carrier.

2. The device of claim 1 wherein the device forms at least part of a cap for a container having at least a partial vacuum.

3. The device of claim 1 wherein the holder comprises 2, 3, 4, 5, or 6 sensing electrodes.

4. The device of claim 1 wherein the electron acceptor is Ruthenium Purple.

5. The device of claim 1 wherein the electrically conductive substrate comprises gold of at least 18 carat purity.

6. The device of claim 1 wherein the electrically conductive substrate comprises a platinum alloy with a 90:10 weight/weight ratio of platinum to iridium.

7. The device of claim 1 wherein the electropolymer matrix comprises a sol-gel.

8. The device of claim 7 wherein the sol-gel comprises a mercaptan containing silane, a bifunctional silane, or a combination thereof.

9. The device of claim 1 wherein the or each sensing electrode includes an intermediate layer between the electron acceptor and the electropolymer matrix or carrier, where the intermediate layer comprises a polyaniline or a derivative thereof comprising one or more non-polar substituents.

10. The device of claim 1 wherein the analytes are biomarkers selected from the group consisting of hypoxanthine, adenosine, ATP, inosine, acetylcholine, choline, glucose, glutamate, lactate, and D-serine, and combinations thereof.

11. The device of claim 1 wherein the biorecognition molecule is an antibody or enzyme.

12. The device of claim 1 wherein the analytes are capable of providing indicators of biochemical abnormalities for use in diagnostic or monitoring purposes or indicators of physiological condition in healthy organisms.

13. The device of claim 1 wherein the holder comprises more than one type of sensing electrode for the analysis of more than one analyte.

14. The device of claim 1, where the device optionally forms at least part of a cap for a container having at least a partial vacuum, or where the device or the cap is optionally included in a kit for the detection of one or more analytes; the kit comprising the device or the cap, and a set of instructions for the detection of the one or more analytes, and where the device, the cap, or the kit is adapted for single or disposable use.

15. A cap for a container having at least a partial vacuum comprising the device of claim 1.

16. A kit for the detection of one or more analytes, the kit comprising the device of claim 1, where the device optionally forms at least part of a cap for a container having at least a partial vacuum; and a set of instructions for detecting the one or more analytes.

17. The kit of claim 16 wherein the one or more analytes are capable of being used for fetal monitoring, stroke monitoring, or schizophrenia diagnosis.

18. A method comprising using the device of claim 1 for detecting one or more analytes, where the device optionally forms at least part of a cap for a container having at least a partial vacuum, or where the device or the cap is optionally included in a kit for the detection of one or more analytes; the kit comprising the device or the cap, and a set of instructions for the detection of the one or more analytes.

19. The method of claim 18 wherein at least one analyte has a half-life in the biological sample of less than 10 min.

20. A process for preparing the device of claim 1, the process comprising:
   i) providing a substrate comprising an electrically conductive substrate surface within a holder;
   ii) depositing a first layer comprising a suitable electron acceptor; and
   iii) depositing a second layer comprising an electropolymer matrix with one or more biorecognition molecules absorbed on or included within said second layer.

* * * * *